US00PP12527P2

(12) United States Plant Patent
Vandenberg et al.

(10) Patent No.: US PP12,527 P2
(45) Date of Patent: Apr. 9, 2002

(54) CHRYSANTHEMUM PLANT NAMED 'YOCARSON CITY'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/594,752

(22) Filed: Jun. 16, 2000

(51) Int. Cl.[7] ..... A01H 5/00

(52) U.S. Cl. ..... Plt./286

(58) Field of Search ..... Plt./286, 295, 298

(56) References Cited

PUBLICATIONS

UPOV–ROM, 2001/03, Plant Variety Database, GTI Jouve Retrieval Software, citation for 'Yocarson City'.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yocarson City', characterized by its upright, somewhat outwardly spreading and uniformly mounded plant habit; vigorous growth habit; freely branching habit; uniform flowering response; early flowering, eight-week response time; floriferousness; daisy-type inflorescences that are about 7.3 cm in diameter; bright red and yellow bicolored ray florets with green disc florets that develop slowly; lack of pollen production; and good postproduction longevity with inflorescences maintaining good substance and color for at least three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Yocarson City.

The new Chrysanthemum is a product of a planned breeding program conducted by the Inventors in Salinas, Calif. and Fort Myers, Fla. The objective of the breeding program is to create new potted Chrysanthemum cultivars with desirable inflorescence form and floret colors and good postproduction longevity.

The new Chrysanthemum originated from a cross made by the Inventors in May, 1993, in Salinas, Calif., of a proprietary Chrysanthemum seedling selection identified as YB-4034 as the female, or seed, parent with the Chrysanthemum cultivar Mobile, disclosed in U.S. Plant Pat. No. 9,335, as the male, or pollen, parent. The new Chrysanthemum was discovered and selected by the Inventors in December, 1996, as a single flowering plant within the progeny of the stated cross grown in a controlled environment in Fort Myers, Fla. The selection of this plant was based on its desirable inflorescence form and floret colors and good postproduction longevity.

Asexual reproduction of the new Chrysanthemum by vegetative tip cuttings was first conducted in Fort Myers, Fla. in February, 1997. Asexual reproduction by cuttings has shown that the unique features of this new Chrysanthemum are stable and reproduced true to type in successive generations.

SUMMARY OF THE INVENTION

The cultivar Yocarson City has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yocarson City'. These characteristics in combination distinguish 'Yocarson City' as a new and distinct Chrysanthemum:

1. Upright, somewhat outwardly spreading and uniformly mounded plant habit.

2. Vigorous growth habit.

3. Freely branching, dense and full plants.

4. Uniform flowering response.

5. Early flowering, eight-week response time.

6. Very freely flowering.

7. Daisy-type inflorescences that are about 7.3 cm in diameter.

8. Bright red and yellow bicolored ray florets with green disc florets that develop slowly.

9. Can be grown as a natural spray-type.

10. Pollen production not observed.

11. Good postproduction longevity with inflorescences maintaining good substance and color for at least three weeks in an interior environment.

Plants of the new Chrysanthemum differ from plants of the parent, cultivar, Mobile, in the following characteristics:

1. Plants of the new Chrysanthemum are denser and not as open in plant form as plants of the cultivar Mobile.

2. Ray floret color of the new Chrysanthemum is brighter and more orange than ray floret color of plants of the cultivar Mobile.

3. Plants of the new Chrysanthemum are more freely flowering than plants of the cultivar Mobile.

4. Plants of the new Chrysanthemum have not been observed to produce pollen whereas plants of the cultivar Mobile produce abundant pollen.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the sheet comprises a top perspective view of a typical flowering plant of 'Yocarson City'.

The photograph at the bottom of the sheet comprises a close-up view of typical inflorescences of the cultivar Yocarson City.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Yocarson City.

Commercial classification: Daisy-type potted Chrysanthemum.

Parentage:

*Female, or seed, parent.*—Proprietary Chrysanthemum seedling selection identified as YB-4034.

*Male, or pollen, parent.*—*Dendranthema grandiflora* cultivar Mobile, disclosed in U.S. Plant Pat. No. 9,335.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy-type potted Chrysanthemum which can be grown as a natural spray-type. Inverted triangle; stems mostly upright and somewhat outwardly spreading giving a uniformly mounded appearance to the plant. Freely branching, about four lateral branches develop after removal of terminal apex (pinching); dense and full plants. Vigorous.

*Plant height.*—About 25 cm.

*Plant width.*—About 35 cm.

*Lateral branches.*—Length: About 16 cm. Diameter: About 3 mm. Internode length: About 1.4 cm. Strength: Strong, flexible. Texture: Pubescent. Color: Slightly darker than 144A.

*Foliage description.*—Arrangement: Alternate. Length: About 5.7 cm. Width: About 4.5 cm. Apex: Cuspidate. Base: Attenuate to truncate. Margin: Palmately lobed, sinuses between lateral lobes divergent to convergent. Texture: Upper and lower surfaces with very fine pubescence; veins prominent on lower surface. Color: Young foliage upper surface: 147A. Young foliage lower surface: 147B. Mature foliage upper surface: 147A. Mature foliage lower surface: 147B. Venation upper surface: 147A. Venation lower surface: 147B. Petiole length: About 2.1 cm. Petiole diameter: About 2 mm. Petiole color: 147A and 147B.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for at least three weeks in an interior environment.

*Quantity of inflorescences.*—Typically grown as a spray-type; about five to six inflorescences per lateral stem, about 20 to 24 inflorescences per plant.

*Inflorescence bud.*—Height: About 6 mm. Diameter: About 7 mm. Color: Close to 147A.

*Inflorescence size.*—Diameter: About 7.3 cm. Depth (height): About 2.5 cm. Diameter of disc: About 1.25 cm. Receptacle diameter: About 5 mm.

*Ray florets.*—Shape: Elongated-oblong. Orientation: Slightly upright, about 20 to 25° from perpendicular to peduncle. Aspect: Straight and flat. Length: About 3.5 cm. Width: About 8 mm. Apex: Acute, emarginate or dentate. Base: Attenuate; short corolla tube. Margin: Entire. Texture: Smooth, glabrous, satiny. Number of ray florets per inflorescence: About 24; two rows. Color: When opening, upper surface: Yellow, close to 9A, and red, close to 46A, bicolored. Base, mostly yellow; mid-section, longitudinally streaked with yellow and red; apex, mostly red. When opening, lower surface: Yellow, 9A to 9B, and dark red, close to 53A, bicolored. Base, mostly yellow; mid-section and apex, longitudinally streaked with yellow and dark red. Fully opened, upper surface: Yellow, 9A, and red, 45A to 46A, bicolored. Base, mostly yellow; mid-section and apex, longitudinally streaked with yellow and red. With development, red becomes more orange, close to 44A. Fully opened, lower surface: Yellow, 9A to 9B, and dark red, close to 53A, bicolored. Base, mostly yellow; mid-section and apex, longitudinally streaked with yellow and dark red.

*Disc florets.*—Shape: Tubular, elongated. Apex: Five-pointed. Length: About 5.5 mm. Width: Apex, about 1.5 mm; base, about 1 mm. Number of disc florets per inflorescence: About 84. Color: Immature: Lighter than 144A; development occurs slowly and green color is maintained. Mature: Apex: 9A. Mid-section: Close to 147C. Base: 155D.

*Peduncles.*—Length: First peduncle: About 3.5 cm. Fourth peduncle: About 5.8 cm. Diameter: About 2 mm. Angle to vertical: About 45° from vertical. Strength: Strong, flexible. Color: 144A.

*Reproductive organs.*—Androecium: Present on disc florets only. Anther color: 9A to 12A. Pollen amount: Pollen production has not been observed. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yocarson City', as illustrated and described.

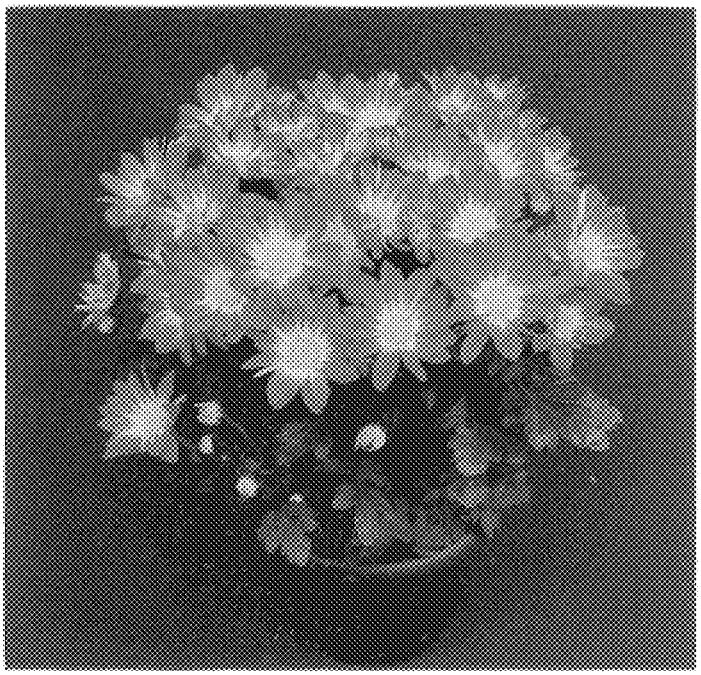
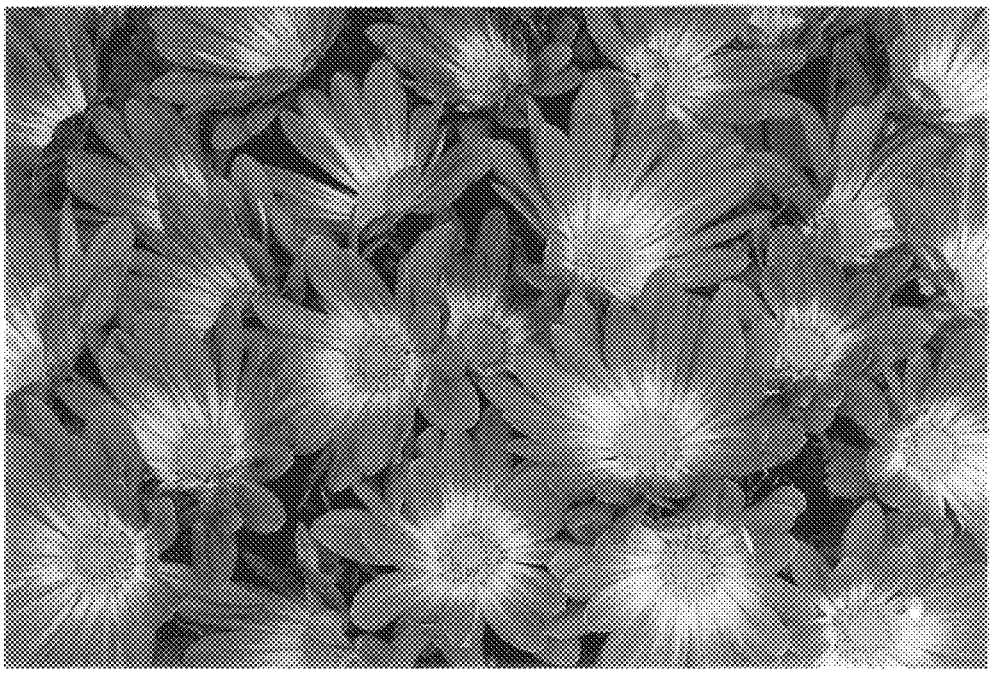

* * * * *